United States Patent
Foster et al.

(10) Patent No.: US 8,871,500 B2
(45) Date of Patent: *Oct. 28, 2014

(54) MEMS PARTICLE SORTING ACTUATOR AND METHOD OF MANUFACTURING

(75) Inventors: John S. Foster, Santa Barbara, CA (US); Daryl W. Grummitt, Santa Barbara, CA (US); John C. Harley, Santa Barbara, CA (US); Jaquelin K. Spong, Falls Church, VA (US); Kimberly L. Turner, Santa Barbara, CA (US)

(73) Assignee: Innovative Micro Technology, Goleta, CA (US)

( * ) Notice: Subject to any disclaimer, the term of this patent is extended or adjusted under 35 U.S.C. 154(b) by 346 days.

This patent is subject to a terminal disclaimer.

(21) Appl. No.: 13/374,898

(22) Filed: Jan. 23, 2012

(65) Prior Publication Data

US 2012/0190104 A1 Jul. 26, 2012

Related U.S. Application Data

(60) Provisional application No. 61/457,170, filed on Jan. 21, 2011.

(51) Int. Cl.
*C12M 1/36* (2006.01)
*C12M 1/38* (2006.01)
*C12M 3/00* (2006.01)
*B01L 3/00* (2006.01)
*C12M 1/00* (2006.01)

(52) U.S. Cl.
CPC .......... *C12M 47/04* (2013.01); *B01L 2400/043* (2013.01); *B01L 2400/0633* (2013.01); *B01L 3/502761* (2013.01); *B01L 2200/0652* (2013.01); *B01L 3/502738* (2013.01)

USPC ................. 435/288.5; 435/288.7; 435/288.3; 435/288.4; 435/305.1; 435/305.2

(58) Field of Classification Search
CPC ................... B01L 3/502738; B01L 3/502761; B01L 2200/0652; B01L 2400/043; B01L 2400/0633
USPC .......... 435/288.7, 288.3, 288.4, 288.5, 305.1, 435/305.2
See application file for complete search history.

(56) References Cited

U.S. PATENT DOCUMENTS

| | | | | |
|---|---|---|---|---|
| 5,837,200 A | * | 11/1998 | Diessel et al. | 422/73 |
| 5,914,262 A | * | 6/1999 | MacMichael et al. | 435/243 |
| 6,332,540 B1 | * | 12/2001 | Paul et al. | 209/3.1 |
| 6,838,056 B2 | | 1/2005 | Foster | |
| 7,220,594 B2 | | 5/2007 | Foster et al. | |
| 7,229,838 B2 | | 6/2007 | Foster et al. | |
| 7,264,972 B2 | | 9/2007 | Foster | |
| 2003/0012657 A1 | * | 1/2003 | Marr et al. | 417/48 |
| 2003/0153085 A1 | * | 8/2003 | Leary et al. | 436/63 |
| 2004/0087984 A1 | | 5/2004 | Kupecki et al. | |

(Continued)

*Primary Examiner* — Nathan Bowers
(74) *Attorney, Agent, or Firm* — Jaquelin K. Spong

(57) ABSTRACT

A MEMS-based system and a method are described for separating a target particle from the remainder of a fluid stream. The system makes use of a unique, microfabricated movable structure formed on a substrate, which moves in a rotary fashion about one or more fixed points, which are all located on one side of the axis of motion. The movable structure is actuated by a separate force-generating apparatus, which is entirely separate from the movable structure formed on its substrate. This allows the movable structure to be entirely submerged in the sample fluid.

18 Claims, 13 Drawing Sheets

(56) References Cited

U.S. PATENT DOCUMENTS

| | | |
|---|---|---|
| 2005/0105077 A1* | 5/2005 | Padmanabhan et al. ........ 356/39 |
| 2006/0040273 A1* | 2/2006 | Chaiken et al. ................... 435/6 |
| 2007/0178529 A1* | 8/2007 | Breidford et al. .............. 435/7.1 |
| 2008/0003142 A1 | 1/2008 | Link et al. |
| 2008/0087584 A1 | 4/2008 | Johnson et al. |
| 2011/0120562 A1* | 5/2011 | Tan et al. ........................... 137/1 |
| 2011/0151498 A1* | 6/2011 | Quake et al. .................... 435/29 |
| 2013/0157283 A1* | 6/2013 | Yung et al. ..................... 435/7.1 |

* cited by examiner

MEMS PARTICLE SORTING ACTUATOR AND METHOD OF MANUFACTURING

CROSS REFERENCE TO RELATED APPLICATIONS

This application claims priority to U.S. Provisional Application No. 61/457,170, filed Jan. 21, 2011 and incorporated by reference herein in its entirety. This application is related to U.S. patent application Ser. No. 13/374,899 filed on Jan. 23, 2014

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for sorting small particles in a fluid stream with a MEMS device.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example.

MEMS devices, in the form of a movable valve, may be used as a sorting mechanism for sorting various particles, such as cells from a fluid stream such as blood. The particles may be transported to the sorting device within the fluid stream enclosed in a microchannel, which flows under pressure. Upon reaching the MEMS sorting device, the sorting device directs the particles of interest to a separate receptacle, and directs the remainder of the fluid stream to a waste receptacle.

A number of patents have been granted which are directed to such MEMS-based particle sorting devices. For example, U.S. Pat. No. 6,838,056 (the '056 patent) is directed to a MEMS-based cell sorting device, U.S. Pat. No. 7,264,972 b1 (the '972 patent) is directed to a micromechanical actuator for a MEMS-based cell sorting device. U.S. Pat. No. 7,220,594 (the '594 patent) is directed to optical structures fabricated with a MEMS cell sorting apparatus, and U.S. Pat. No. 7,229,838 (the '838 patent) is directed to an actuation mechanism for operating a MEMS-based particle sorting system. Each of these patents is hereby incorporated by reference, and each is assigned to Innovative Micro Technology, assignee of the present invention.

MEMS-based cell sorter systems may have substantial advantages over existing fluorescence-activated cell sorting systems (FACS) known as flow cytometers. These systems are generally large and expensive. They sort particles based on a fluorescence signal from a tag affixed to the cell of interest. The cells diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

SUMMARY

A system and method are described for separating particles of interest from the remainder of a fluid stream using a MEMS device. The system may make use of a unique micromechanical MEMS actuator which may improve the speed, simplicity and manufacturability of the particle sorting system. A particle sorting system based on this MEMS actuator is described. In contrast to existing FACS flow cytometers, the MEMS-based cell sorter does not rely on a sheath fluid, and does not atomize the droplets containing the target cells. As a result, the MEMS-based cell sorting system can sort rare cells such as cancer cells or tumor cells, sperm cells, or other particles with outstanding speed and precision, and a very high proportion of the cells (>95%) are viable after sorting. The system is small, inexpensive and requires virtually no sterilization as the components in contact with the sample fluid are discarded after use.

The MEMS actuator is substantially different in design from prior art cell sorting devices. The design includes a movable structure which has much lower inertia, much faster actuation, and is completely submerged in fluid. It makes use of an external force-generating apparatus which produces a force which arises in and acts over nearly the entirety of the movable structure in the MEMS actuator, unlike prior art designs. In the embodiments described here, the nature of the force is magnetostatic, however, it should be understood that other phenomena may be used, including electrostatic forces, to move the movable MEMS structure. In the embodiment described here, the MEMS cell sorting system distinguishes and sorts the target particle from the other components of the fluid stream based on a fluorescence signal from the particles. However, it should be understood that other phenomena may be used to distinguish particles, including electrical, mechanical, hydrodynamic, mass, and other properties that may vary between particles.

The novel MEMS actuator may include a plurality of microfabricated fluidic channels formed in a plane of the substrate and a movable structure with a motion substantially in the plane, acted on by a force substantially in the same plane and wherein the movable structure simultaneously opens a first microfabricated fluidic channel which is in the plane and closes a second microfabricated fluidic channel also in the plane. The MEMS actuator may also have have an axis substantially parallel to the motion of the movable structure, wherein that motion is about one or more fixed points, and wherein the one or more fixed points are all located on one side of the axis, and wherein the movable structure moves from a first position to a second position in response to a force arising within the movable structure itself, without direct mechanical coupling to a force generating apparatus, and wherein the movable structure opens a microfabricated fluid passage on the other side of the axis from the fixed points when the movable structure moves to the second position in response to the force. Because of the unique architecture of the device, it may operate while being entirely submerged in fluid, because the force-generating mechanism may be completely detached from the MEMS actuator.

These and other features and advantages are described in, or are apparent from, the following detailed description.

BRIEF DESCRIPTION OF THE DRAWINGS

Various exemplary details are described with reference to the following figures, wherein:

In FIG. 2a the actuator is in the first (default) position, in FIG. 2b the actuator is in the second (sort) position;

DETAILED DESCRIPTION

The system described herein is a MEMS based particle sorting system which may make use of a unique micromechanical actuator design. The actuator design may improve the speed, precision, cost and manufacturability of the system, compared to prior art systems. In the figures to follow, similar reference numbers are intended to refer to similar structures, and the structures are illustrated at various levels of detail to give a clear view of the important features of this novel device.

In the figures discussed below, similar reference numbers are intended to refer to similar structures, and the structures are illustrated at various levels of detail to give a clear view of the important features of this novel device.

Figure 1:
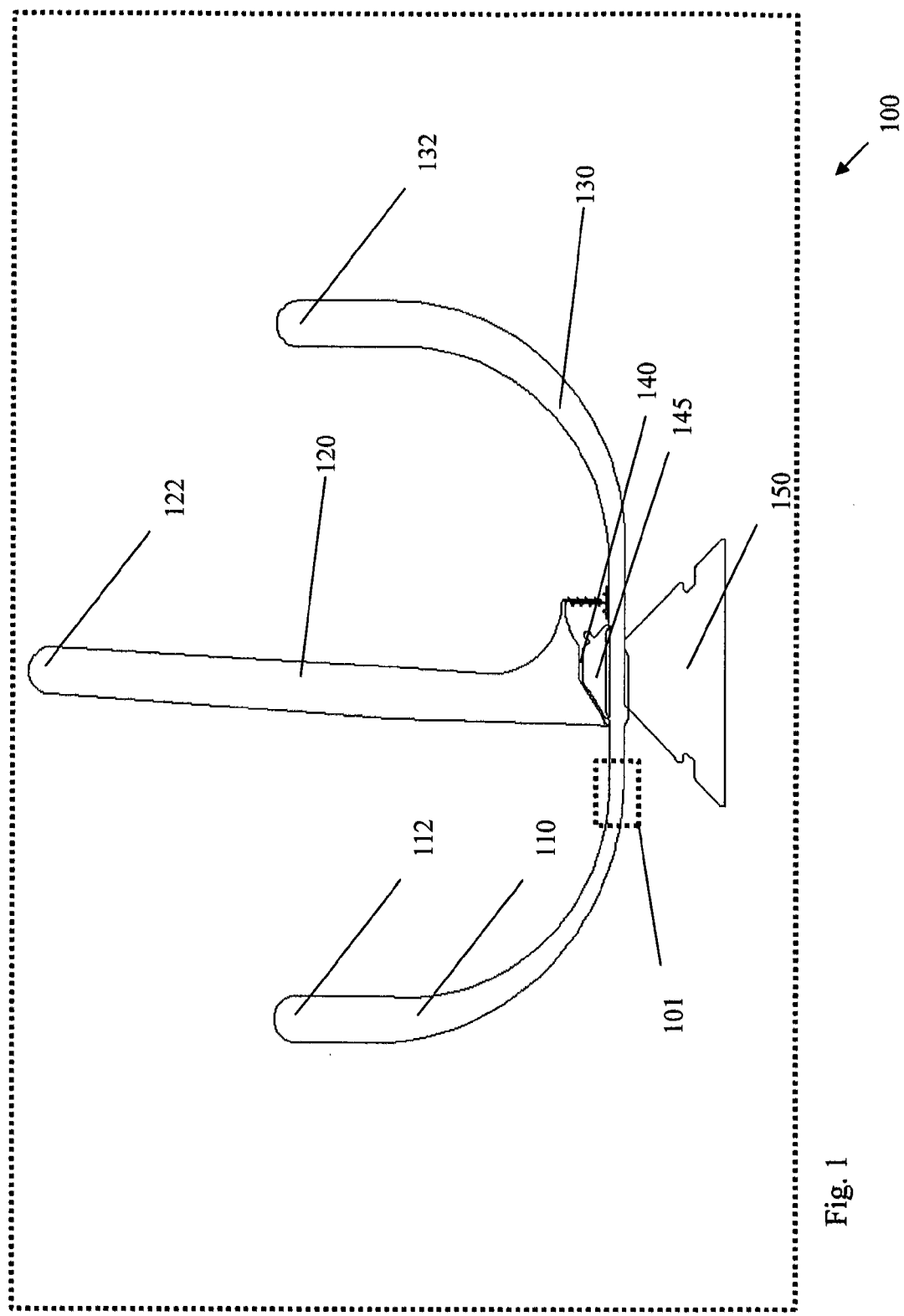
FIG. 1 is schematic illustration of a novel MEMS particle sorting actuator in a MEMS particle sorting system with a detection region that distinguishes the target particle from other components of the fluid stream.

FIG. 1 is a schematic illustration of the MEMS particle sorting actuator, which is usable in the MEMS particle sorting system described below. The area designated 100 refers to a portion of a semiconductor substrate that includes a microfabricated device, that is, area 100 is a semiconductor chip containing the microfabricated sorting mechanism. The substrate or chip 100 also defines a plane in which the microdevice is fabricated, as well as the plane in which the microdevice moves. The motion and fabrication plane is generally parallel to the surface of the substrate 100, and in the plane of the paper.

The substrate or chip 100 may also include a plurality of small fluidic channels 110, 120 and 130 formed in the substrate 100. The fluidic channels allow a fluid sample stream to flow therein, wherein the fluid stream may contain a multitude of particles, some of which are to be separated from the others, forming a purified sample at the output. The channels may include an input channel 110 which admits the sample fluid from an input port 112, the sort channel 120 which directs the sorted target particles into a sort reservoir 122, and a waste channel 130 which allows all the non-target particles to flow through the device to be collected in a waste reservoir 132. Examples of target particles may include stem cells, cancer cells, bacteria, blood cells, sperm cells, lymphocytes, T-cells, for example. The fluid stream may be blood, lymph, semen, saline or dilute samples of these fluids, for example. The substrate or chip 100 may be covered by an optically transparent, flat layer which enclosed the fluidic channels 110, 120 and 130, while allowing light to pass through this layer.

While in the fluid stream, the components of the sample may pass through a detection region 101, and past the movable structure 140 of the MEMS actuator, which either diverts the stream into the sort channel 120 and reservoir 122, or allows it to pass to the waste channel 130 and reservoir 132. The chip 100 may include areas 145 and 150 into which a permeable magnetic material has been inlaid, whose function is described more fully below.

In the detection region 101, the target particle may be distinguished from the other constituents of the fluid sample. The detection means may be, but is not necessarily, a microfabricated structure located in the input channel 120 upstream of the movable structure 140. The detection means may be based on any number of characteristics or attributes that distinguish the target particle from the others in the fluid stream. For example, the particles may be distinguished by, for example, differences in their mechanical, electrical, optical, magnetic, hydrodynamic, mass, electrostatic, magnetostatic or photovoltaic properties, to name just a few. This list is not meant to be exhaustive, but instead to provide examples of detection systems which may be used with the actuator described herein.

In one embodiment, the target particle may be a particular cell which may be tagged with a fluorescent tag, which emits a photon of a particular color when irradiated by a laser at a particular wavelength. Such tags are well known in the field and include for example fluorescein, Texas Red, phycobiliproteins, cyanine derivatives and rhodamine. While much of this disclosure is directed to this application, it should be understood that the systems and methods described herein are also applicable to other detection mechanisms used to distinguish particles one from another. These mechanisms may be well known, or may yet be invented.

Upon passing through the detection region 101, a signal is generated by the detector (not shown) indicating that a target particle is present in the detection region. After a known delay, a signal is generated by a controller which indicates that the sorting gate, i.e. the movable structure 140, is to be opened, in order to separate the target particle which was detected, from the other components in the fluid stream. When this signal is generated, a force is generated between the flap-like movable structure 140 and a fixed feature 150, which draws the flap-like movable structure 140 towards the fixed feature 150. This motion closes off waste channel 130 and waste receptacle 132, and redirects the target particle into a sort receptacle 122 at the end of sort passage 120. The sorted sample is subsequently collected from receptacle 122.

Figure 2A:
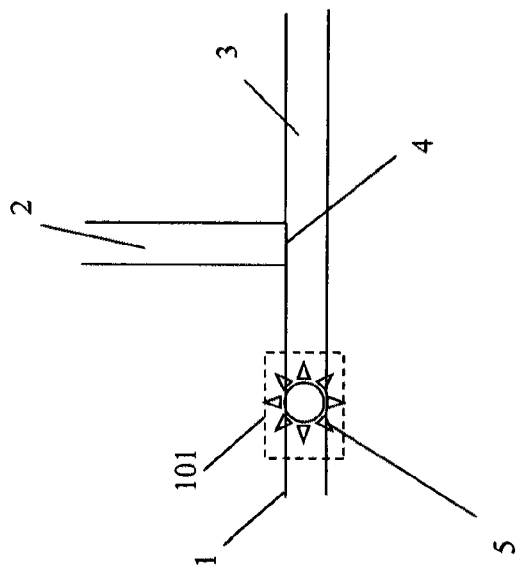
FIG. 2a is a simplified illustration of the MEMS actuator in the MEMS particle sorting system, showing an exemplary out-of-plane detection mechanism which distinguishes a particle of interest from other constituents of the fluid sample.
Figure 2B:
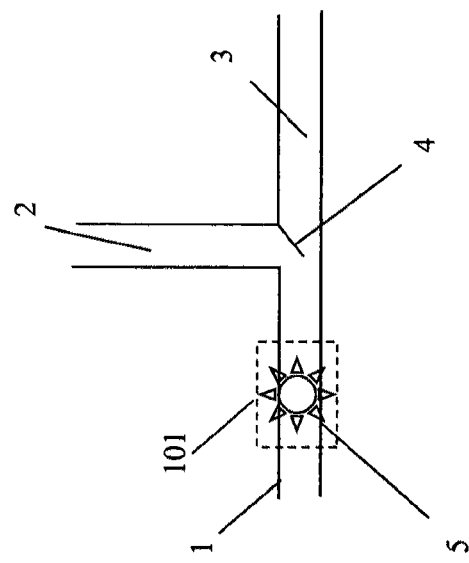

FIG. 2 is a more generic illustration of the sorting system shown in FIG. 1. FIG. 2 is intended to make clear the relative location of the detection region and motion of the microfabricated flap 4 with respect to the flow through the system. Flap 4 shown in FIG. 2 corresponds to flap 140 shown in FIG. 1.

The sample may be input into detection region 101 through the input passage 1 shown. The sample may be a blood sample which has been diluted with fetal calf serum or buffy, for example. Importantly, the flow of the sample from input channel 1, past detection region 101 to sort channel 2 or waste channel 4 through the sorter valve 4, is all in the same plane, which is the fabrication plane of the sorter valve 4 and the plane of motion of the sorter valve 4. In other words, the novel MEMS actuator 100 may include a plurality of microfabricated fluidic channels formed in a plane of the substrate and a movable structure 140 with a motion substantially in the plane, acted on by a force substantially in the same plane and wherein the movable structure simultaneously opens a first microfabricated fluidic channel which is in the plane and closes a second microfabricated fluidic channel also in the plane. This is in contrast to the device described in the incorporated '056, '972, '594 and '838 patents, in which the flow is through a vertical channel above the sorting diverter. Because the irradiation and scattered light detection is generally orthogonal to the solid surfaces in the device, grazing incidence reflections are reduced and thus noise sources that would otherwise interfere with detection are reduced or eliminated.

In one embodiment, the cells in the sample may have been tagged with a fluorescent tag and input to the system by flowing through input passage 1. A laser source 5 may be located in the orthogonal plane to this plane of flow, and the detector may also be orthogonally located. The beams from the laser and the detected light may be collinear, and separated using appropriate dichroic mirrors as will be further described below. Accordingly, the laser and the detector may share an optical path which is oriented substantially perpendicularly to this plane.

Figure 3:
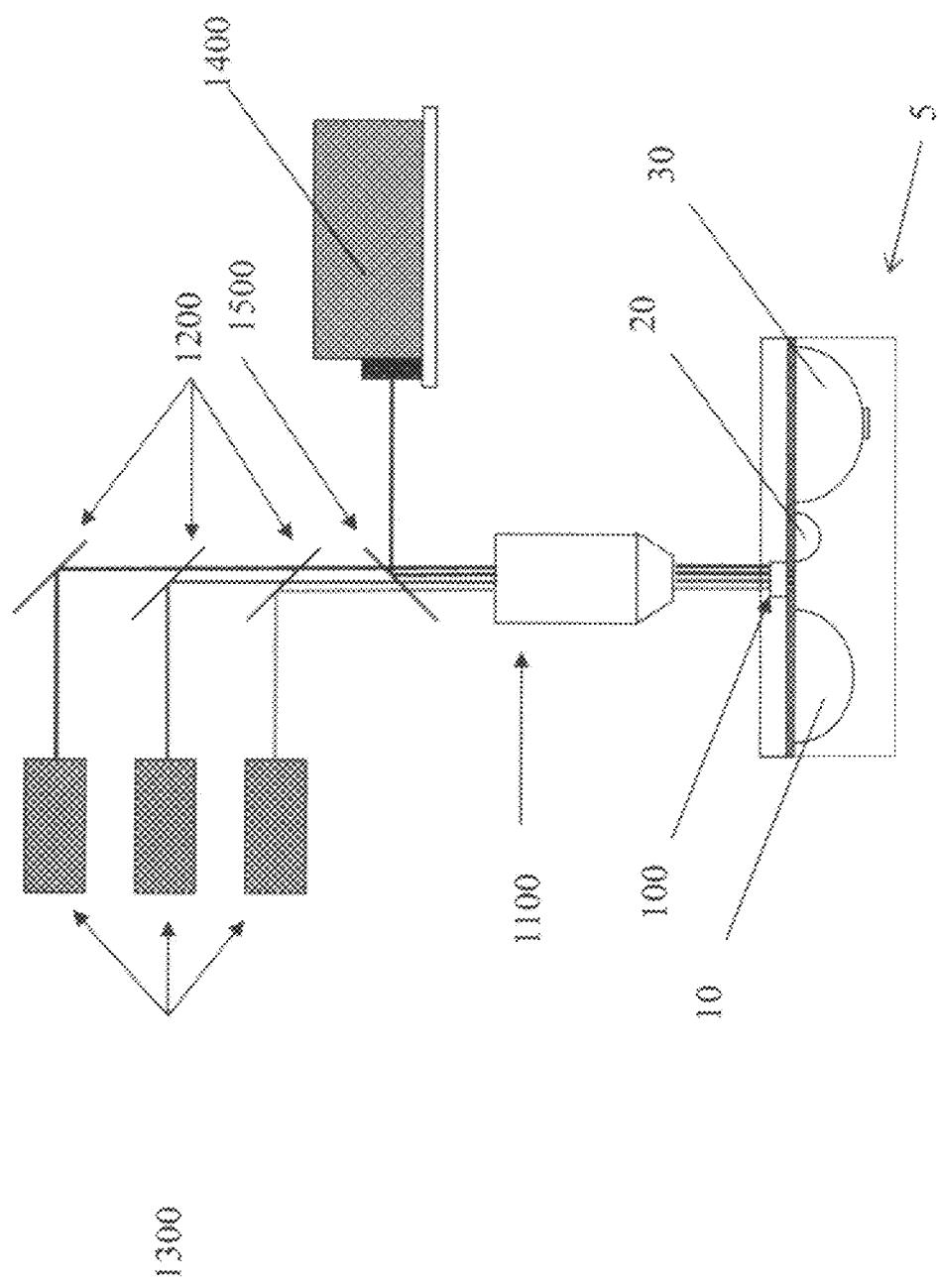
FIG. 3 is a schematic illustration of embodiment of the MEMS actuator in the MEMS particle sorting system, showing other components of the detection system and the removable cartridge containing the sample and fluid flow.

FIG. 3 is a more detailed illustration of one embodiment of the particle sorting system using the microfabricated flap valve movable structure 140. Reference number 5 refers to a disposable, self-contained cartridge that houses a sample reservoir 10, a sort reservoir 20 and waste reservoir 30, which are in fluid communication with input channel 10, sort channel 20 and waste channel 30 shown in FIG. 1. The MEMS chip 100 containing the MEMS actuator 140 may be disposed in the front of this cartridge 5 as shown in FIG. 3. The disposable cartridge is described more fully in co-pending U.S. patent application Ser. No. 13/374,899, filed on Jan. 23, 2014. This cartridge 5 may be disposed in a system such that a laser and detector are situated directly adjacent to the detection region shown in FIGS. 1 and 2.

As mentioned previously, a laser source 1400 may be directed by a turning mirror 1500 through the detection optics 1100 onto the device surface 100 perpendicular to the fabrication plane and the plane of motion of the sorter flap 40 and 140. The fluorescence emitted from the irradiated particles may be shaped by detection optics 1100 and separated by dichroic mirrors 1200 and directed into a bank of photodetectors 1300. A plurality of photodetectors may accommodate multiple wavelengths of emitted light, for multiparametric detection. The signal output by the photodetectors 1300 indicates the presence or absence of the target particle in the detection region 101. Upon detection of the target particle, a signal is generated by a controller (not shown) which energizes a force-generating or flux-generating apparatus. The force- or flux-generating apparatus is a device which causes a force to arise in the movable structure itself, causing the motion of the movable structure toward the force-generating apparatus, which has an equal and opposite force arise therein. In general, this force-generating apparatus is not directly mechanically coupled to the movable structure 140. The force arises in the flap or movable structure, pulling the flap or movable structure toward the force-generating apparatus, opening the sort channel 20 and 120 to the flow and closing the waste channel 30 and 130. In one embodiment, this force-generating apparatus is a source of magnetic flux, for example an electromagnet, which is energized to produce a magnetic flux from a current-carrying coil. The flap or movable structure 140 is formed substantially from a permeable magnetic material, such as nickel-iron permalloy, which is drawn toward the gradient of this magnetic flux as is well known from elementary magnetostatics. This force pulls the flap or movable structure 140 toward the force-generating apparatus, redirecting the target particle from the waste path 130 to the sort path 120.

The description now turns to a detailed discussion of the motion of the movable structure, the force-generating apparatus which causes the motion, the nature of the motion, and the novel characteristics thereof.

Figure 4:
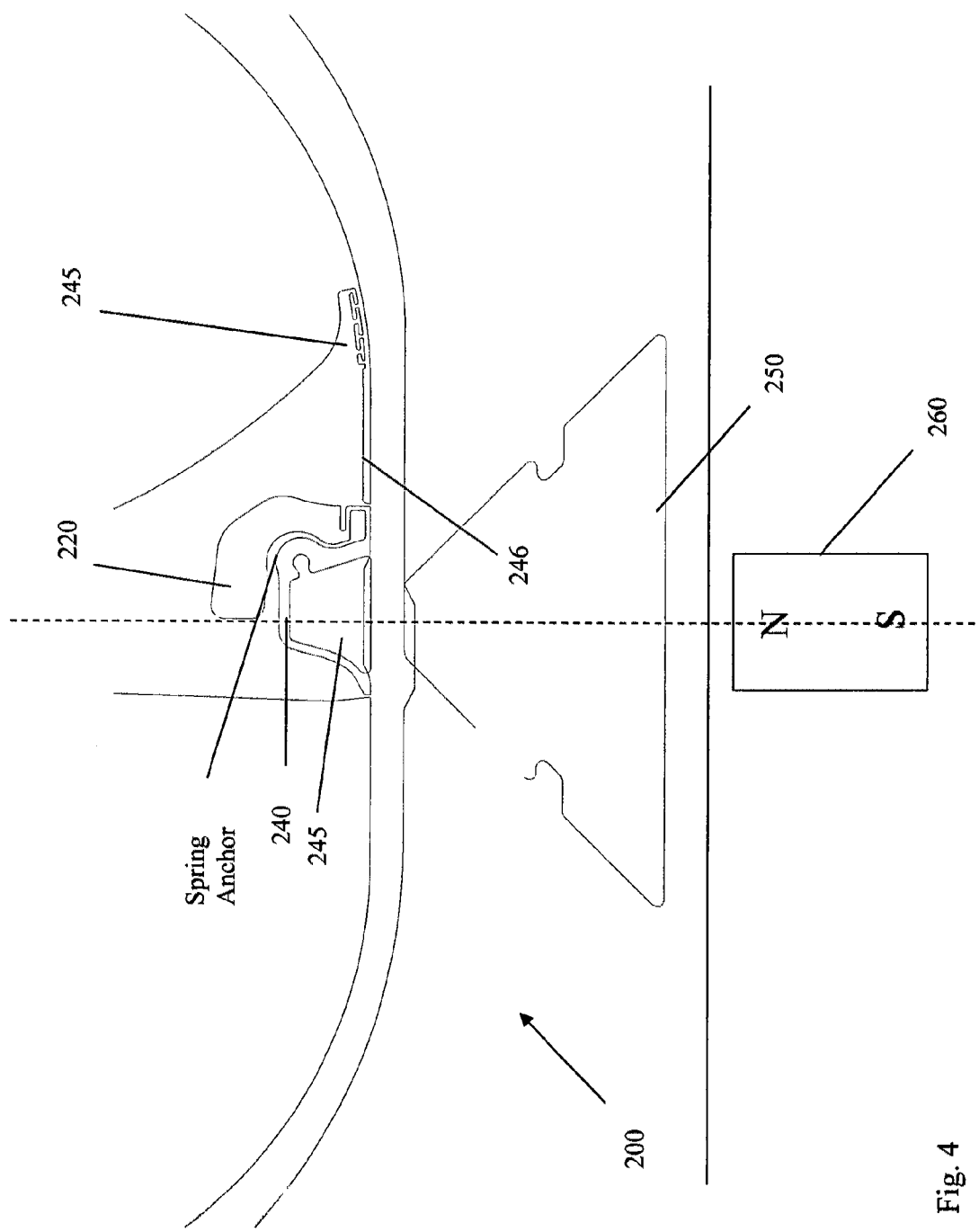
FIG. 4 is an enlarged view of the first embodiment of the MEMS actuator in the MEMS particle sorting system, with the actuator in the first (default) position adjacent to an external magnet.

FIG. 4 is view of an embodiment of the micromechanical actuator 200 shown in FIG. 1, and it relationship to a force-generating apparatus 260. In FIG. 4, the micromechanical actuator 200 is in the first position, which is the default or waste position, wherein the sample stream from the input channel 210 flows directly to the waste channel 230, bypassing the sort channel 220.

The device illustrated in FIG. 4 is similar to the device 100 shown in FIG. 1, and like numbers refer to like features. The term "force-generating apparatus" should be understood to mean a device or structure which causes a force to be exerted on the movable structure 140. The nature of the force may be, for example, electrostatic or magnetostatic, which can take place across a distance which separates the force-generating apparatus 260 from the movable structure 240.

The movable structure 240 may include an area 245 into which a permeable magnetic material 245 has been inlaid. Another area of inlaid magnetic material 250 may be formed adjacent to the movable structure 240. Manufacturing details for the fabrication of this structure and for inlaying the magnetic material may be found in the aforementioned '056, '972, '594 and '838 patents. The magnetic material 245 may be inlaid in the movable structure 240 to a substantial depth, that is, the ratio of the depth of the magnetic material 245 to its characteristic width may be at least about 1.2×. Such a ratio may enhance the pull down force while keeping the channel dimensions small. It is the presence of this permeable material 245 which may render the movable structure 240 susceptible to the influence of the force-generating apparatus 260. One distinguishing feature of this device is that the force that arises between the movable structure 240 and the force generating apparatus 260 arises within the movable structure itself by virtue of the permeable material 245, rather than in some adjoining or coupled structure. Accordingly, the pull down force arises within a substantial portion, that is within at least 50% of the area or volume, of the movable structure itself. Said another way, the movable structure is, itself, the armature of the motor formed by structures 250 and an external source of magnetic flux.

The channel dimensions in the vicinity of the movable structure may define essentially a rectangular cross section, consistent with the dimensions of the movable structure 240. The cross sectional dimensions may be on the order of 30 microns and with a channel depth to channel width aspect ratio greater than 1.2:1.

The motion of the movable structure 240 may be defined by its points of attachment to the substrate. In particular, if the motion of the movable structure 240 is substantially along an axis at any given point in time, the points of attachment may all be on one side of this axis. This axis is shown as the dotted vertical line in FIGS. 4 and 5. As a result, the motion of the movable structure tends to pivot about one side, thereby opening up an unobstructed pathway on the other side of the axis. Motion "substantially parallel to" or "substantially along an axis" should be understood to mean motion such that the angle between the vector of motion and the axis is less than 45 degrees at any given point in time. Because of this architecture, the movable structure is exceptionally small and has low inertia, and very low drag. But because the forces arising can be substantial, as described next, the movable structure can open and close the fluidic pathway exceedingly quickly, on the order of 25 usec. The motion can be predominantly linear or predominantly rotary, depending on how the movable structure 240 is attached to the substrate at the fixed points. An embodiment of each of these approaches is described below.

As mentioned previously, the movable structures 240 and 245 may also be located adjacent to another permeable magnetic structure 250. The adjacent magnetic material 250 may have a tapered outline, narrower at the top than the bottom as shown in FIG. 4. This outline may serve to shape the lines of flux that will be applied to it, so as to enhance their gradient in the narrow tapered region. This may have the effect of enhancing the force that will arise between the tapered magnetic region and the permeable portion 245 of the movable structure 240.

The force that causes the movement of the movable structure 240 may arise over a substantial portion of the movable structure, in response to a force generating apparatus located adjacent to the movable structure 240 and adjacent permeable structure 250. An exemplary force-generating apparatus is shown in FIG. 4. In FIG. 4, the movable structures 240 and 245 are located adjacent to an external source of magnetic flux, which constitutes the force-generating apparatus 260. Importantly, this force-generating apparatus 260 may be entirely separable from and external to, the substrate 200 as indicated by the boundary line shown. The coupling between the force-generating apparatus 260 and the movable structure 240 may be magnetic, so that no direct mechanical connection is necessary. This allows the whole movable structure 240 to be submerged in fluid and sealed from the outside world and flux generating apparatus 260. Accordingly, the entire movable structure may be submerged in the sample fluid, and the sample fluid may flow past the movable structure without the addition of a sheath fluid. A sheath fluid is a liquid stream in a FAC flow cytometer, which carries and aligns the cells so that they pass single file through the light beam for sensing. The separate force-generating or flux-generating apparatus may also reduce the cost associated with the MEMS actuator 200, as the force-generating apparatus may be used with many MEMS actuators 200.

This force-generating apparatus 260 may be, for example, an electromagnet such as a permeable magnetic core around which a coil of current-carrying conductor is wound. The coil may be energized in response to a signal generated by the detection means 101 shown in FIG. 1. The coil may be wrapped around a simple bar of permeable material, such that a magnetic dipole arises in the bar, with lines of flux emanating from the north pole and returning (in the far field) to the south pole as shown in FIG. 4. This bar-type of flux source may be compatible with the single adjacent permeable feature 250, but other embodiments, described below, may use a horse-shoe shaped electromagnet with the two poles adjacent one another and the magnetic flux traveling between the poles. Additional features of such a force-generating apparatus, and its construction, may be found in the incorporated '838 patent.

Figure 5:
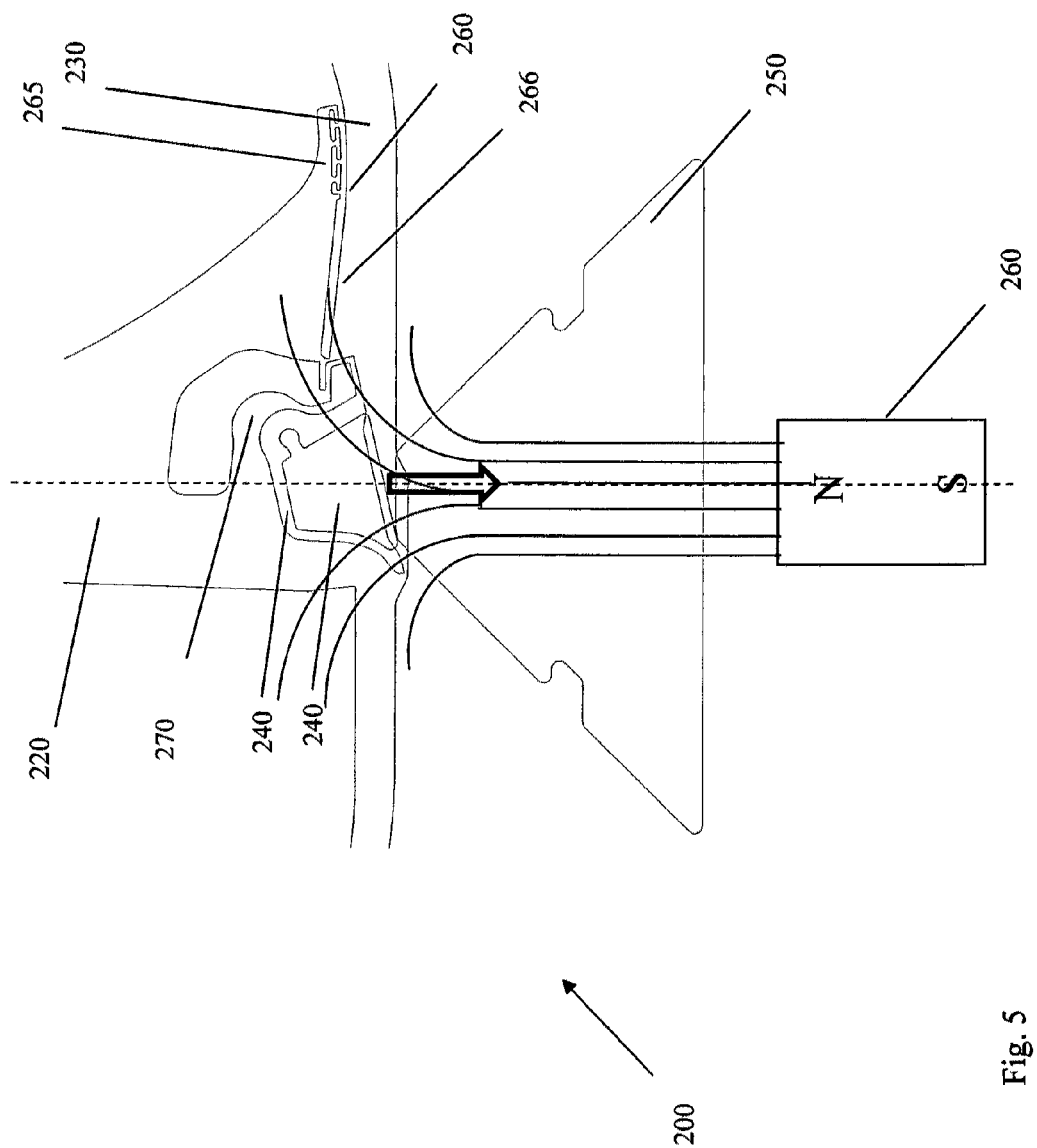
FIG. 5 is an enlarged view of the MEMS actuator in the MEMS particle sorting system, with the actuator in the second (sort) position as the external magnet is energized.

FIG. 5 is a detailed view of the micromechanical actuator in the sort position. In this figure, the flux source, or force generating portion 260 has been energized, such that flux is produced at its north pole. Since lines of magnetic flux find the lowest reluctance path to the south pole of the magnet, the lines are preferentially drawn into the permeable material, and focused in the vicinity of the tapered end of the magnetically permeable adjacent structure 250. They exit this structure 250 with high density and quickly disperse. The magnetically permeable portion 245 of the movable structure 240 is drawn toward this region of denser flux, pulling the magnet down and drawing the movable structure toward the adjacent magnetic structure 250. The magnetic force arising draws the movable structure from a first position (FIG. 4) in which the sort channel 220 is blocked and the default or waste channel 230 is open, to a second position wherein the sort channel 220 is open and the default channel is closed. This opens the fluidic pathway on the side of the movable structure (i.e. the sort channel 220) opposite the fixed points. A target particle, having been identified as such by in the detection region, is thereby diverted into the sort channel 220 by the action of energizing the electromagnet 260. The actuation force may be on the order of milliNewtons arising from a magnetomotive force (MMF) of about 25 ampere-turns in the force-generating apparatus 260. The total throw of the MEMS movable structure 240 may be about 25 microns, and this motion may take place in about 25 usec.

When the current to the coil of the force-generating apparatus 260 is discontinued, a spring force arising from flexible attachment 270 returns the movable structure 240 to its first position, closing the sort channel 220 and opening again the waste channel 230. The restoring force of this spring is designed to be on the order of about 100 N/m, so that the milliNewton actuation force is resisted by a comparable restoring force when the movable structure is deflected by 10-50 microns, in order to return the movable structure 240 to its first position in about 25 usec.

Another unique features of the MEMS actuator 200 is the use of a sympathetic beam 260. The sympathetic beam 260 may include a rigid portion 266 and attached to a flexible hinge 265, that attaches the rigid portion 266 to the substrate 200. When the movable structure 240 moves to its second position, the rigid portion of the sympathetic beam moves up, opening an area directly downstream of the movable structure 240. The large channel formed by the rigid portion allows fluid to be pushed into the larger area, rather than down the length of the waste channel 230. Accordingly, there is less fluid resistance offered to the movable structure as it moves from the first position to the second position. Accordingly, the sympathetic beam expands a fluid region directly downstream of the movable structure, allowing fluid to flow into the expanded region when the movable structure moves in response to the force. This reduces the force required to actuate the movable structure and the increases the actuation speed of the device. The hinge region 265 may be an area with material removed in a pattern around the rigid portion 266, so that the beam may flex generally in the region 265, allowing the sympathetic beam 260 to move. In analogy to electromagnetic signals, the sympathetic beams may act as a "capacitive element" countering the "inductive" nature of the fluid.

Figure 6:
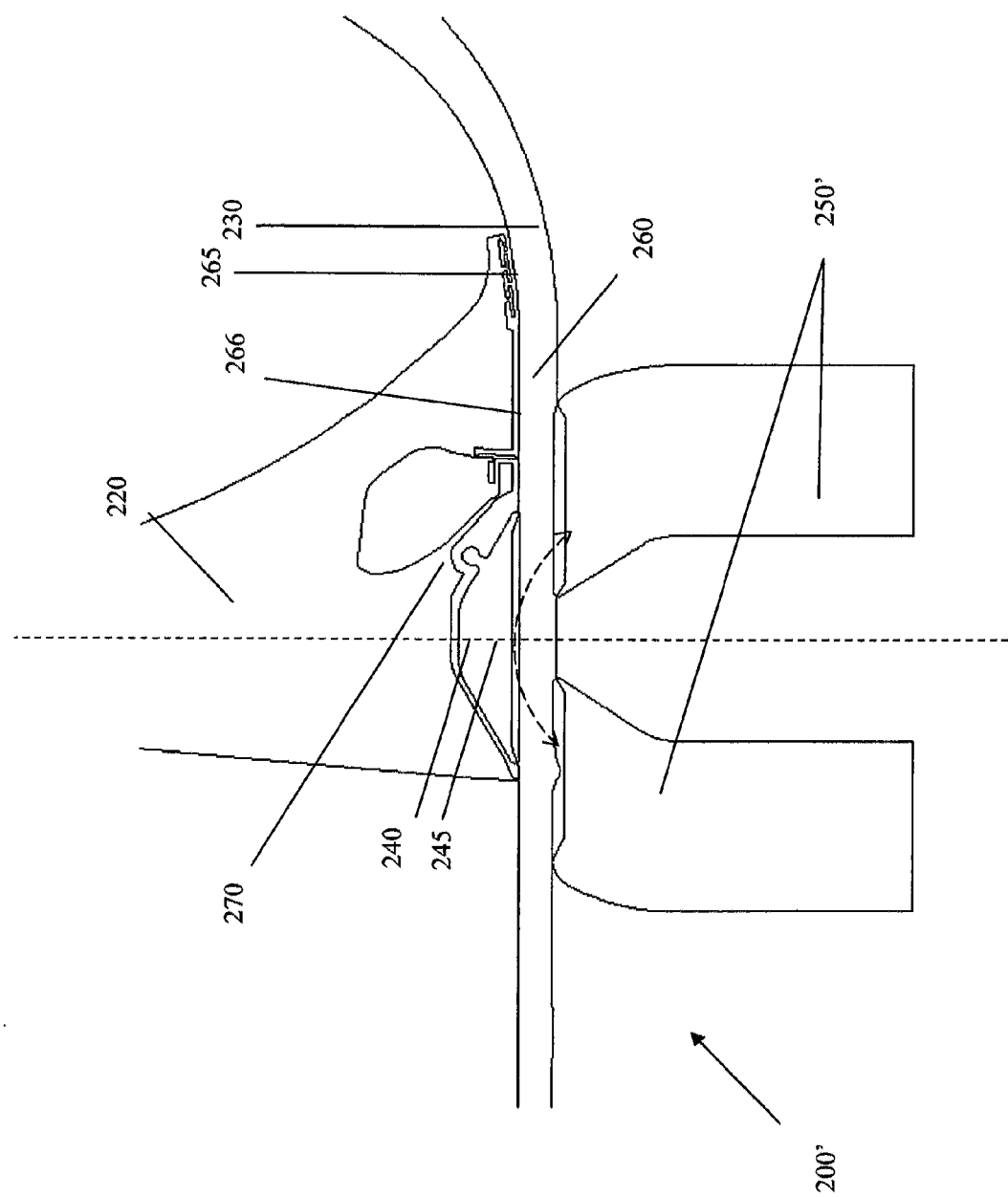
FIG. 6 is an enlarged view of a second embodiment of the MEMS actuator in the MEMS particle sorting system.

FIG. 6 is an enlarged view of a second embodiment of the MEMS actuator in the MEMS particle sorting system. This embodiment is similar to the embodiment depicted in FIGS. 1, 4 and 5 except that instead of a single tapered permeable fixed feature 250, a pair of permeable fixed features 250' are used. These permeable structures may be disposed substantially parallel to one another and substantially symmetrically about the axis of the movable structure. The axis is shown as a dashed line in FIG. 6. These features route the flux from the force-generating apparatus 260 up to the region of the movable structure 240 and concentrate the flux across the gap between the pair of permeable structures 250', as indicated by the dashed arrow in the figure. This embodiment may be particularly compatible with a double-poled, horseshoe type magnet such as that disclosed in the incorporated '838 patent. This embodiment may require less flux to be produced by the force-generating apparatus 260 to produce the same force on the movable portion, and so may operate at lower current with improved reliability. One advantage of this embodiment is a more efficient routing of flux, and so less current needs to be used to gain magnetic saturation of the materials. However, the embodiment may require more precise alignment of external magnetic field in order to drive the flux in and out of the appropriate pole.

Figure 7:
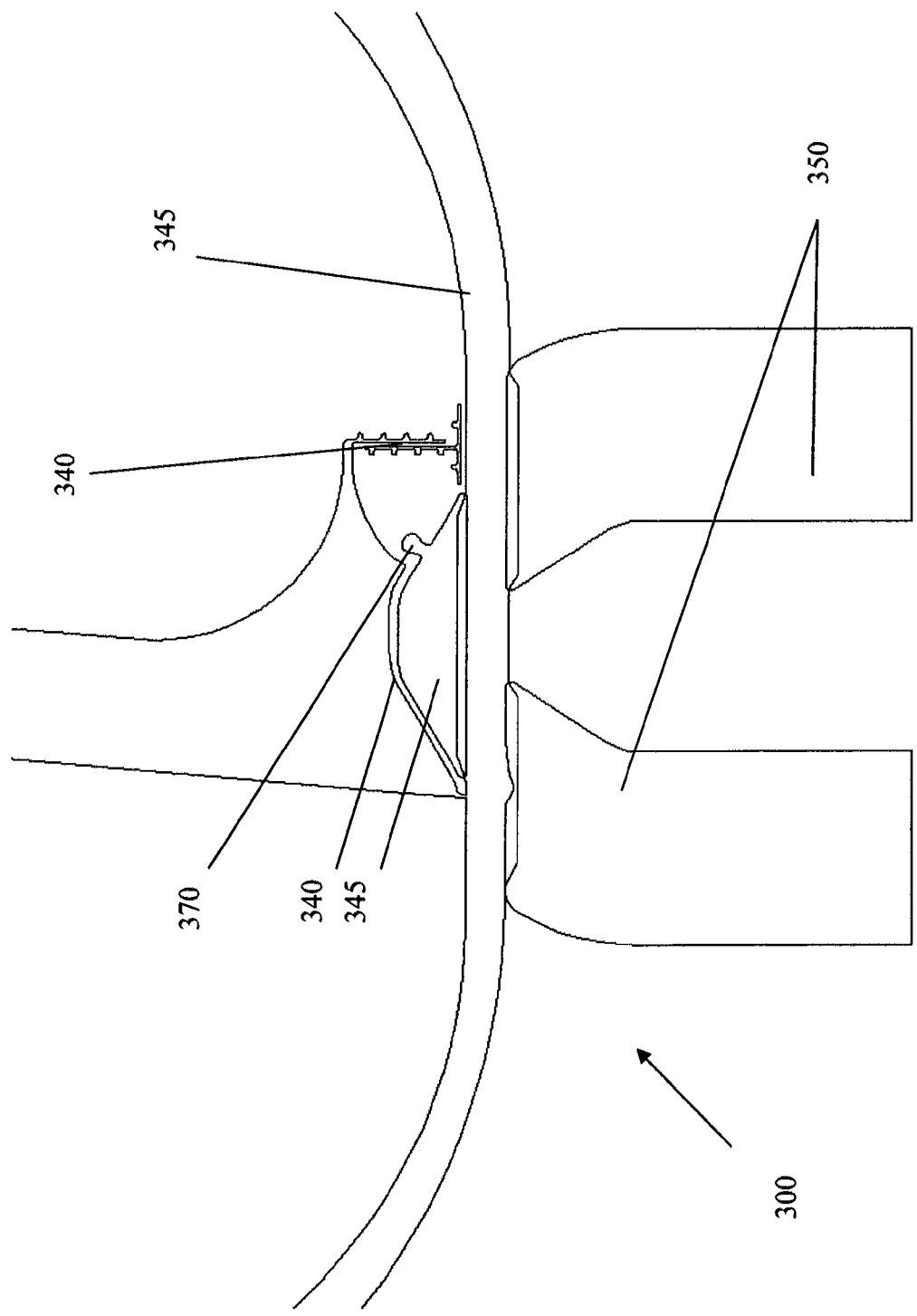
FIG. 7 is an enlarged view of third embodiment of the MEMS actuator in the MEMS particle sorting system.

FIG. 7 is an enlarged view of a third embodiment of the MEMS actuator in the MEMS particle sorting system. This embodiment is similar to the embodiment depicted in FIGS. 1, 4 and 5 except that there is no sympathetic beam 266 and the hinge structure 340 is somewhat different as a result. In the embodiment shown in FIG. 7, the hinge structure 340 is designed to provide a restoring force to the movable structure 340, returning it to its first position as shown in the figure, after actuation during a sort event. The restoring force of this spring is designed to be on the order of about 100 N/m, so that the milliNewton actuation force is resisted by a comparable restoring force when the movable structure is deflected by 10-50 microns, in order to return the movable structure 340 to its first position in about 25 usec. This embodiment also uses the double-pole permeable structure 350, so may also be compatible with the horseshoe-type magnet disclosed in the '838 patent. One advantage of this embodiment is that more force can be generated compared to the rotary actuator, and the damping of the motion may be more easily controlled. However, this embodiment may require a more complex flexure arrangement, and very high damping at the limit of motion may slow the actuation time.

Figure 8:
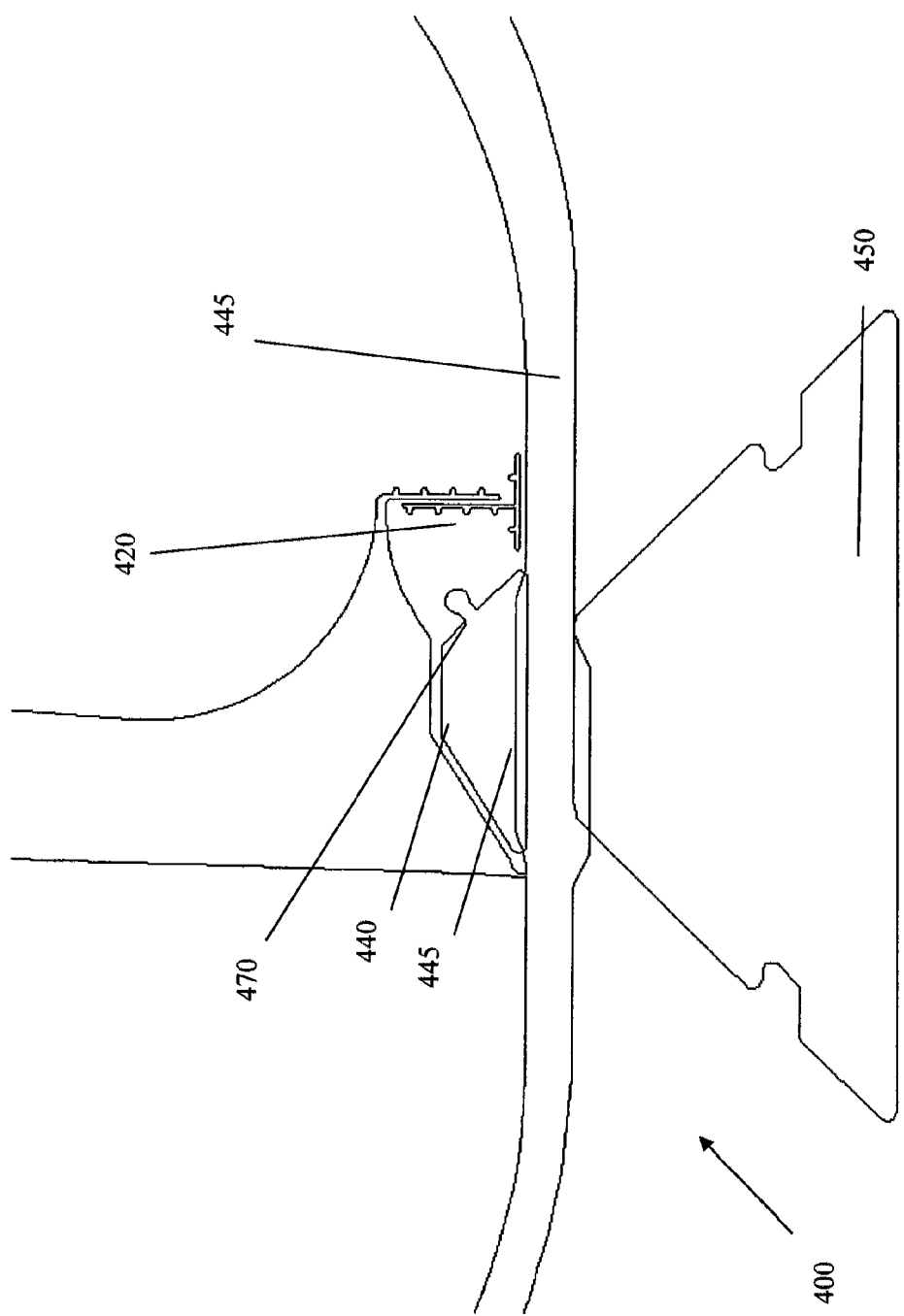
FIG. 8 is an enlarged view of fourth embodiment of the MEMS actuator in the MEMS particle sorting system.

FIG. 8 is an enlarged view of a fourth embodiment of the MEMS actuator in the MEMS particle sorting system. This embodiment is similar to the embodiment depicted in FIG. 7, except that is uses a single tapered permeable fixed feature 450, rather than the pair of permeable fixed features 250'. As with the previous embodiment, there is no sympathetic beam in this embodiment. Since the design does not use a sympathetic beam, the whole device and spring 470 may be stiffer and more robust. However, the speed may be limited because the actuator is required to push the fluid down the length of the channel 445 in order to move to its second position. Thus the actuation force is resisted by the fluid friction within the narrow tube. This embodiment may be compatible with the straight bar type electromagnet as described with respect to FIG. 5. This embodiment with the single taper pole allows a large input area solenoid (force-generating apparatus) to be used to drive the magnetic field without tight alignment tolerances between the external magnet of the force-generating apparatus and the fixed feature 450.

Figure 9:
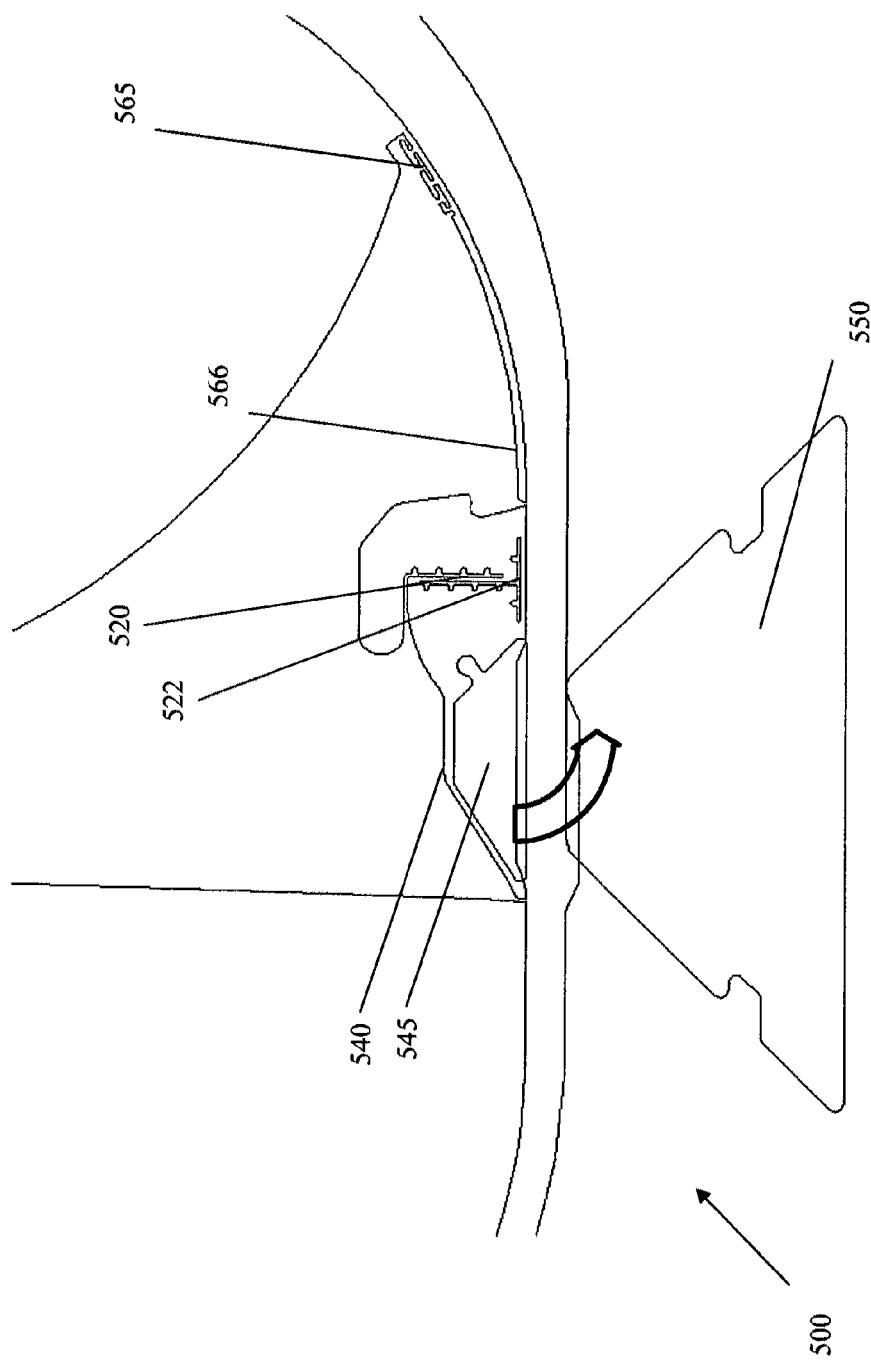
FIG. 9 is an enlarged view of fifth embodiment of the MEMS actuator in the MEMS particle sorting system.

FIG. 9 is an enlarged view of a fifth embodiment of the MEMS actuator in the MEMS particle sorting system. This embodiment is similar to that depicted in FIG. 8, except that it includes a sympathetic spring 565 and associated hinge 566. The sympathetic spring acts similarly to that shown in FIG. 5, wherein upon actuation of the movable structure 540, the sympathetic spring 565 moves up, to clear an area for fluid to move which is very near the movable structure. For this reason, there is less resistance offered to the motion of the movable structure 540 by the fluid, so that the movable structure 540 can move faster and/or with less force. This increases the speed, and/or reduces the current requirements and may improve the reliability of the device. The hinge region 565 is an area with material removed in a pattern around the beam 566, so that the beam may flex generally in the region 565, allowing the sympathetic beam to move.

In the embodiment shown in FIG. 9, a second hinge, 520, may allow the pivoting or rotary motion of the movable structure substantially about a single point, the anchor point of the hinge at the lower region, denoted by 522 in FIG. 9. Although this rotation may not be literally about a single point and thus the motion may not be strictly rotary, the fixed point or points still fall on one side of the axis of motion as described above with respect to FIG. 5.

Figure 10:
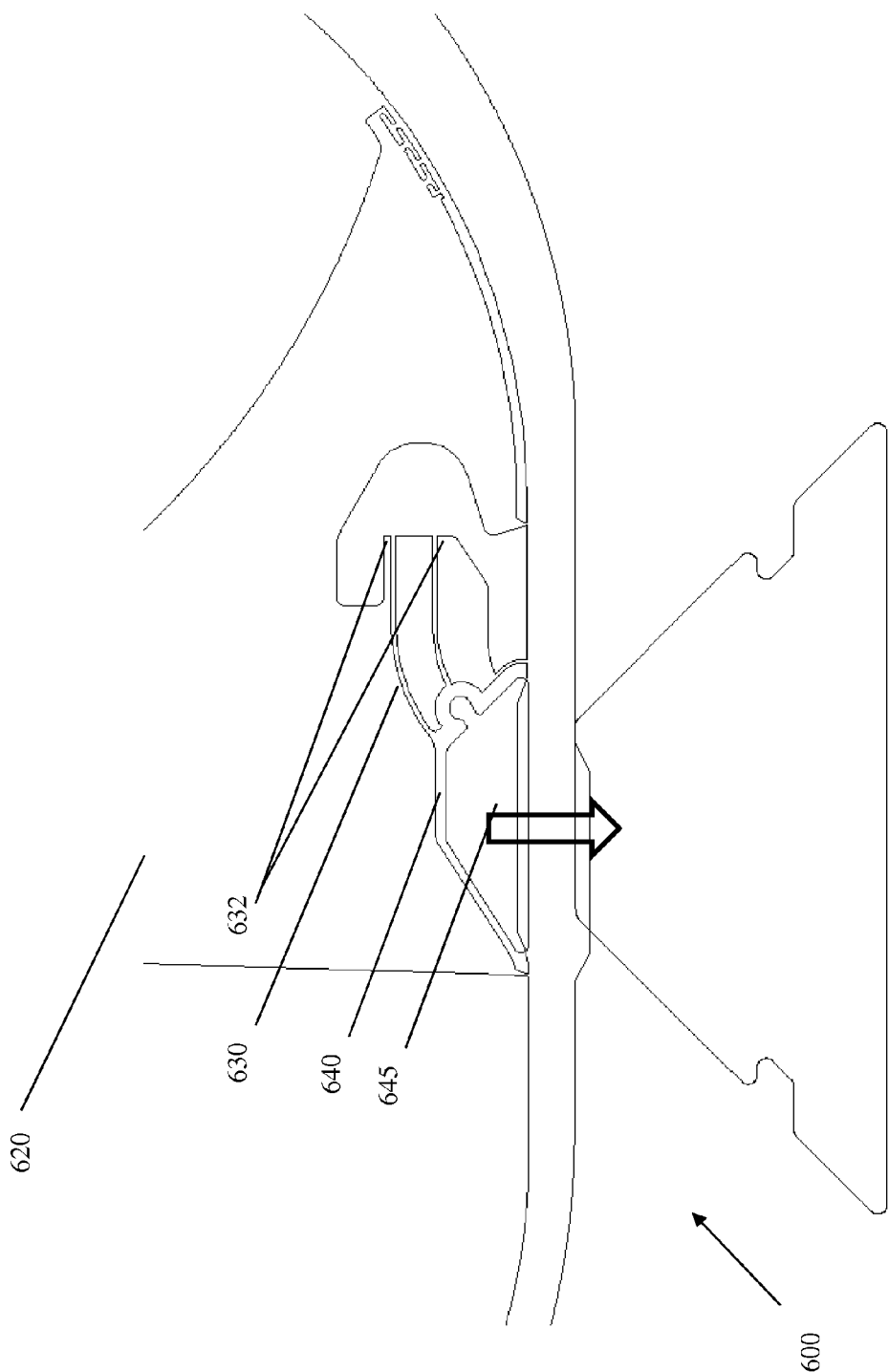
FIG. 10 is an enlarged view of sixth embodiment of the MEMS actuator in the MEMS particle sorting system.

FIG. 10 is an enlarged view of a sixth embodiment of the MEMS actuator in the MEMS particle sorting system. This embodiment is similar to that shown in FIG. 9, except that the motion is substantially linear and about a plurality of fixed points. In FIG. 10, the movable structure 640 is constrained to move approximately linearly because of tethers 630 attaching it to the wall of the substrate. These tethers are attached to two or more fixed points 632, allowing the movable structure 640 to move generally up and down according to the direction shown in FIG. 10. As with the previous embodiments, when the movable structure 640 moves from a first position to a second position about fixed points 632, the movable structure 640 opens up a clear, unobstructed passageway into the sort channel 620, on the side of the axis opposite the fixed points 632. The linear motion actuators shown in FIG. 10, as well as in FIGS. 11-13, can provide more force over the stroke and more damping of the motion, but may be slower to actuate with much more fluidic drag at the end of the range of motion than the rotary-type actuators shown in FIGS. 1, 2 and 4-8.

Figure 11:
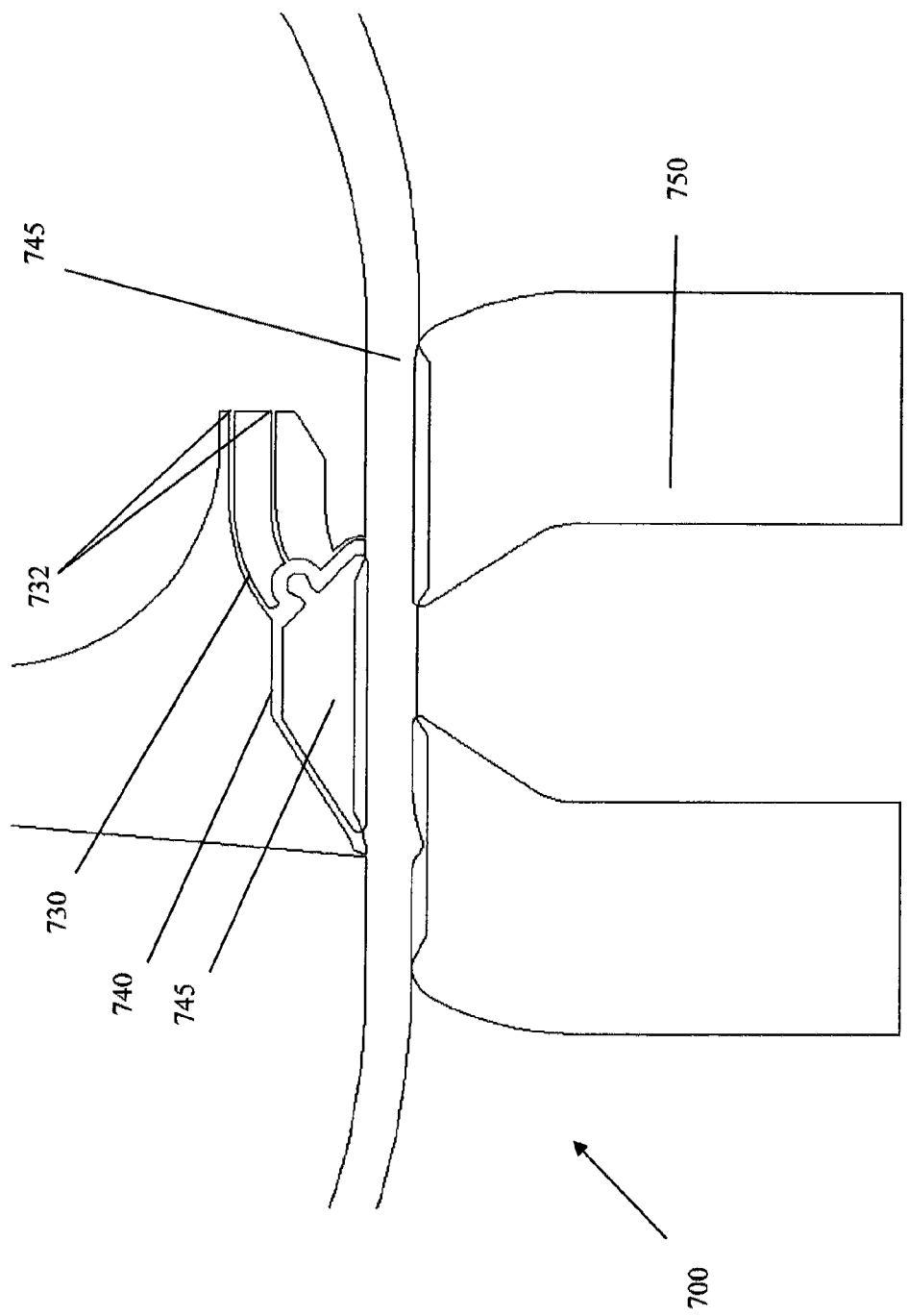
FIG. 11 is an enlarged view of seventh embodiment of the MEMS actuator in the MEMS particle sorting system.

FIG. 11 is an enlarged view of a seventh embodiment of the MEMS actuator in the MEMS particle sorting system. This embodiment is similar to that shown in FIG. 10, with the movable portion 740 tethered to two fixed points. Thus like this embodiment shown in FIG. 10, the movable structure 740 is constrained to move approximately linearly because of tethers 730 attaching it to the wall of the substrate. These tethers are attached to two or more fixed points 732, allowing the movable structure 740 to move generally up and down according to the direction shown in FIG. 11.

However, like the embodiment shown in FIGS. 6 and 7, instead of a single tapered permeable feature 250, a pair of permeable features 750 may be used. These features route the flux from the force-generating apparatus 260 up to the region of the movable structure 740 and concentrate the flux across the gap between the pair of permeable structures 750. This embodiment may be particularly compatible with a double-poled, horseshoe type magnet such as that disclosed in U.S. Pat. No. 7,229,838. There is also no sympathetic beam in this embodiment.

Figure 12:
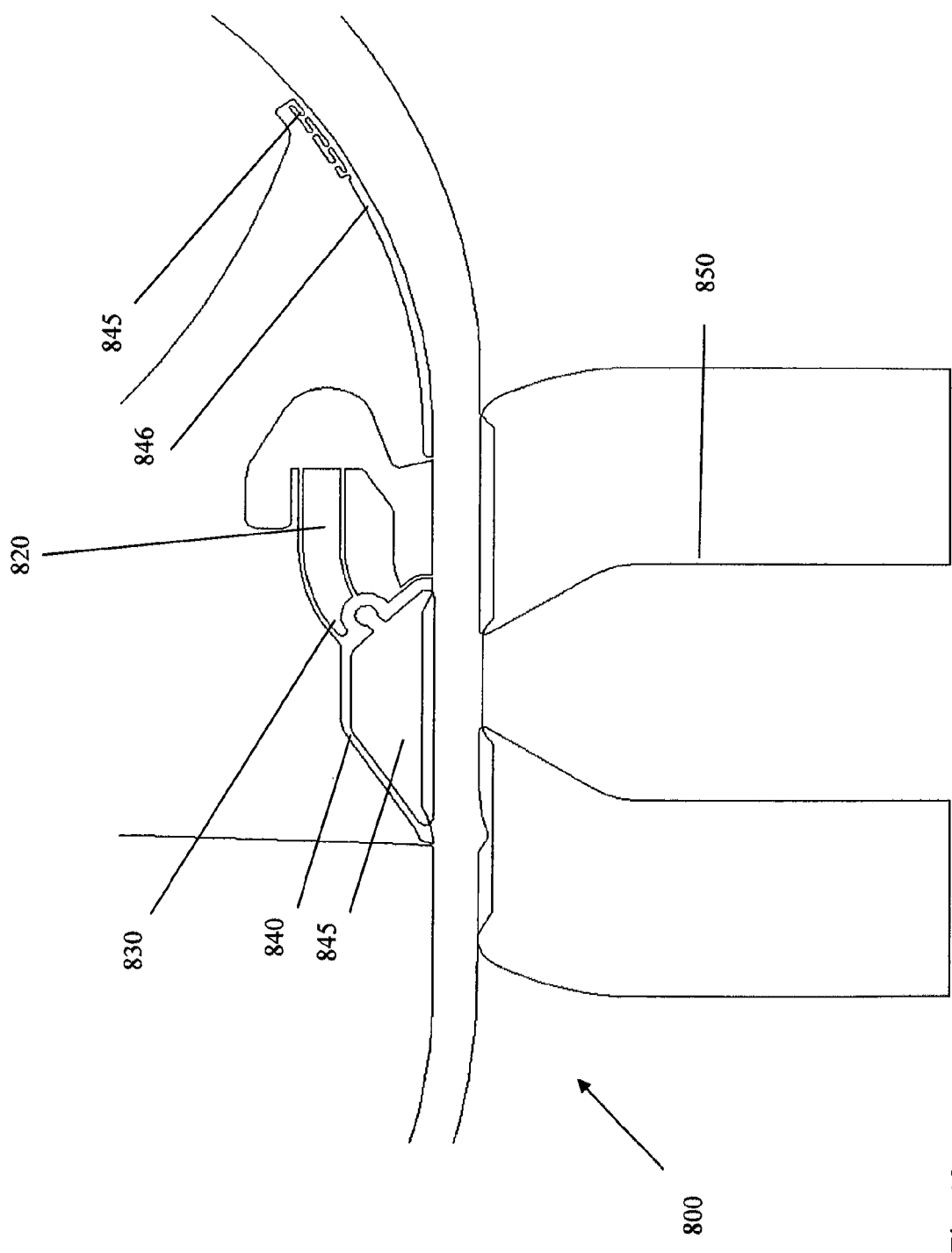
FIG. 12 is an enlarged view of an eighth embodiment of the MEMS actuator in the MEMS particle sorting system.

FIG. 12 is an enlarged view of a eighth embodiment of the MEMS actuator in the MEMS particle sorting system. The embodiment shown in FIG. 12 is similar to that shown in FIG. 11, except that in this embodiment, a sympathetic beam 846 is included. In addition, this embodiment has the multiple tethers 830 attaching the movable structure 840 to fixed points 832, and thus the movable structure 840 moves generally linearly downward toward the pair of permeable structures 850. Thus, this embodiment has the pair of permeable structures 850 rather than the single tapered structure.

Figure 13:
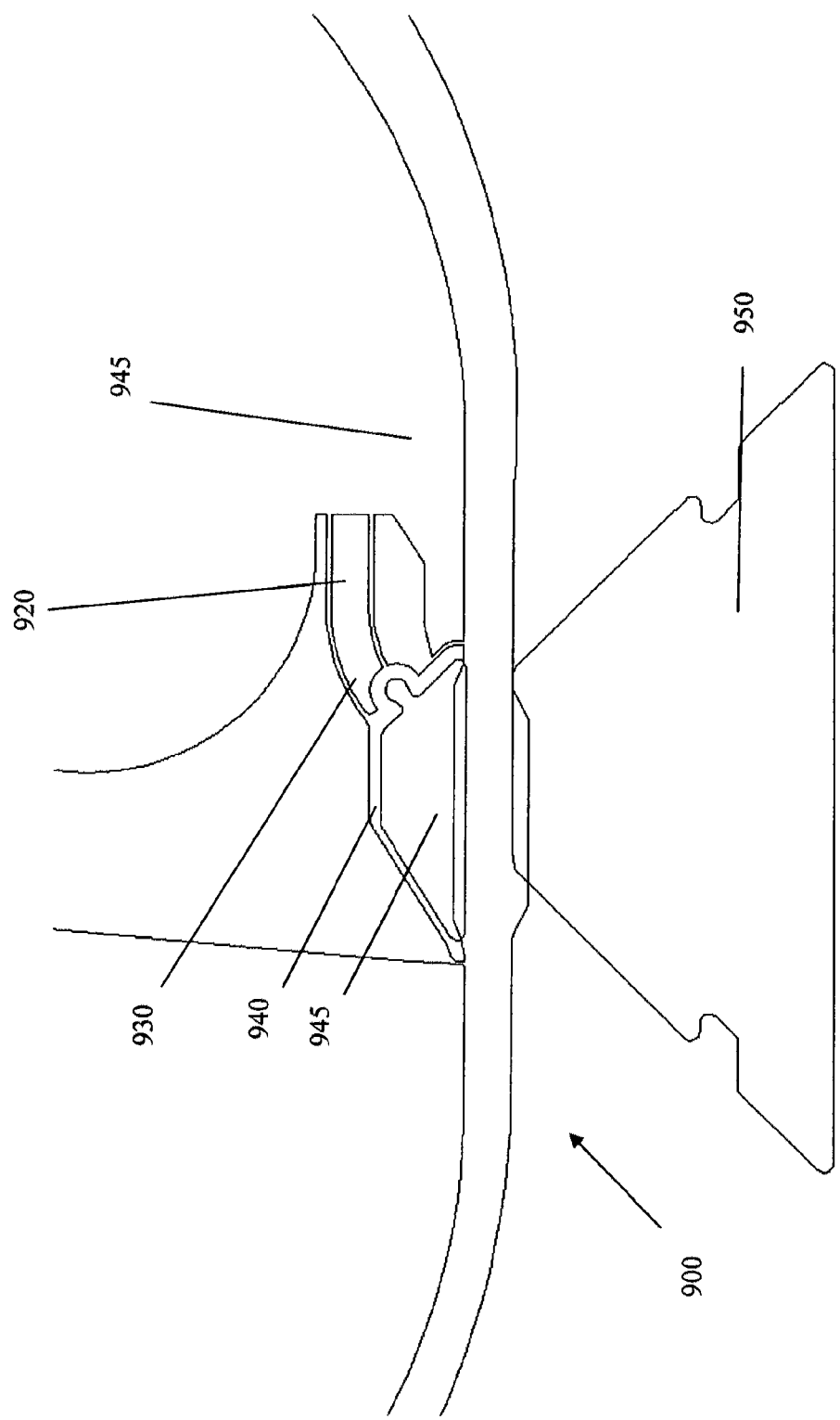
FIG. 13 is an enlarged view of a ninth embodiment of the MEMS actuator in the MEMS particle sorting system.

FIG. 13 is an enlarged view of a ninth embodiment of the MEMS actuator in the MEMS particle sorting system. This embodiment is similar to that shown in FIG. 12, except that no sympathetic beam is included. This embodiment has two fixed points on one side of the axis of motion, and thus the movable structure moves generally linearly downward. This embodiment also uses the single, tapered magnetically permeable structure 950 to focus the magnetic flux in the vicinity of the taper, drawing the permeable inlaid material 945 of the movable structure 940 toward the tapered structure 950 when the external force-generating apparatus is activated.

It should be understood from the foregoing that the various unique features of the novel MEMS actuator may be mixed and matched in various ways, according to the requirements of the application. No particular arrangement of the parts and features of the MEMS actuator are required to practice this invention, which is limited only by the appended claims.

Thus, the unique actuation mechanism, may have the following distinguishing features depicted in FIGS. 1-13, over the prior art, and particularly over the devices disclosed in the aforementioned '056, '972, '594 and '838 patents:
1. Illumination and fluorescence detection may be out-of-plane of the flow, interrogation position and detection may take place in the same plane;
2. Illumination and fluorescence detection may be in the orthogonal plane as flow, and orthogonal to the sorting plane (actuation motion plane)
3. Actuator may be entirely submerged in fluid
4. Actuator motion may be rotary or linear
5. Actuator may only attach to the substrate on one side of the axis of motion
6. Actuator motion can be a combination of translation and rotation about one side
7. The valve mechanism may be the motor armature itself.
8. In one embodiment, a permeable magnetic material works to focus a large external field from one pole of an electromagnet into a small point. The gradient of the field lines as they return to the external coil's far-field pole is what provides the force necessary to move the actuator. Other embodiments may use a sufficiently large external field that no focusing is needed and the focusing element may be omitted. Other embodiments use a pair of permeable elements to focus the flux in the gap between the pair of elements;
9. Sympathetic beams, not directly driven, may serve to reduce the transient inertia and viscous drag of the fluid flow as the actuator is driven. This leads to much higher speed actuations. The sympathetic actuator acts as a "capacitive element" countering the "inductive" nature of the fluid.
10. The actuator may use a substantially straight channel with cross sectional dimensions on the order of 30 microns and with a channel width to channel depth aspect ratio either greater than 1.2:1.

Any and all of the aforementioned MEMS actuators 100-900 may be fabricated by deep reactive ion etching the appropriate pattern in the active (device) layer of a silicon-on-insulator (SOI) substrate, after formation of the magnetizable portions of the microactuators 145-945. The silicon-in-insulator substrate may include a 625 µm silicon "handle" wafer, coated with a 1 µm thick layer of silicon dioxide, followed by a 50 µm "active" or "device" silicon layer. Details regarding the manufacturing and assembly processes of devices similar to structures 140-940 may be found in the incorporated '056, '972, '594 and '838 patents, and are outlined briefly below.

The magnetizable portions of the microactuators 400 and 500 may first be made by depositing a thin metallic seed layer, such as chromium (Cr) and gold (Au) and depositing photoresist over the seed layer. The photoresist may then be patterned according to the shapes of the magnetizable features 145-945 and 150-950 of microactuators 140-940. Finally, a magnetically permeable material with high saturation magnetization such as NiFe permalloy (70-80% Ni, 30-20% Fe) may be plated onto the patterned photoresist and seed layer, forming the magnetically permeable structures 145-945 and 150-950. The photoresist and non-plated portions of the seed layer may then be removed, and the structure planarized by chemical mechanical polishing. An etch mask may subsequently cover the permalloy structures to avoid etching them during the formation of the remainder of the micromechanical actuator using deep reactive ion etching, for example, as described in the aforementioned '056 patent.

The movable structures 140-940 may then be etched into the "device" layer of the SOI wafer. Deep reactive ion etching may form vertical walls needed to precisely define the shape of the movable structure 140-940. After etching the movable structure 140-940, it may be released from the thicker handle layer by etching the insulating layer beneath the movable structure 140-940. At this point, the movable structure is free to move relative to the handle layer. The fluidic channels may then be enclosed by gluing a flat, optical cover to the SOI wafer to form a wafer assembly. The wafer assembly can then be diced to form the individual devices 100-900. These devices may then be installed in a sort system cartridge as shown in FIG. 3 and described more fully in co-pending U.S. patent application Ser. No. 13/374,899, filed on Jan 23, 2014.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:
1. A microfabricated particle sorting actuator capable of motion and fabricated on a layer of a substrate, comprising:
a plurality of microfabricated fluidic channels formed in a plane of the layer of the substrate; and
a movable structure formed in and from the layer of the substrate with a motion substantially in the plane, acted on by a magnetic force substantially in the same plane and wherein the movable structure simultaneously opens a first microfabricated fluidic channel which is in the plane and closes a second microfabricated fluidic channel also in the plane wherein the motion is substantially rotary, and the movable structure is attached to the substrate at one or more fixed points, and further comprising one or more flexible springs attached to the one or more fixed points, which return the movable structure to a first position when the force is removed.

2. The microfabricated particle sorting actuator of claim 1, wherein the movable structure is substantially surrounded by the same fluid which is within the microfabricated fluidic passages.

3. The microfabricated particle sorting actuator of claim 1, further comprising a magnetically permeable material inlaid into the movable structure, wherein the magnetically permeable material moves in response to a flux generating apparatus disposed outside the substrate.

4. The microfabricated particle sorting actuator of claim 1, wherein the movable structure has an axis substantially parallel to the motion of the movable structure, wherein that motion is about one or more fixed points, and wherein the one or more fixed points are all located on one side of the axis, and wherein the movable structure moves from a first position to a second position in response to a force arising within the movable structure itself, without mechanical coupling to a force-generating apparatus, and wherein the movable structure opens the first microfabricated fluidic passage when in the second position, when the movable structure moves in response to the force, and wherein the movable structure and microfabricated fluidic passages are all disposed substantially in the plane.

5. The microfabricated particle sorting actuator of claim 1, wherein the motion is substantially linear, and the movable structure is attached to the substrate at two or more fixed points.

6. The microfabricated particle sorting actuator of claim 4, further comprising at least one magnetically permeable fixed feature inlaid into the layer of the substrate, adjacent to the movable structure and shaped to concentrate lines of magnetic flux in the vicinity of the movable structure.

7. The microfabricated particle sorting actuator of claim 6, wherein the at least one magnetically permeable fixed feature comprises at least one of a single magnetically permeable fixed feature with a tapered shape and two magnetically permeable fixed features disposed substantially parallel to one another and substantially symmetrically about the axis of the movable structure.

8. The microfabricated particle sorting actuator of claim 1, further comprising at least one beam, which expands a fluid region directly downstream of the movable structure, allowing fluid to flow into the expanded fluid region when the movable structure moves in response to the force.

9. The microfabricated particle sorting actuator of claim 1, wherein the entire movable structure is submerged in a sample fluid, and the sample fluid flows past the movable structure without the addition of a sheath fluid.

10. The microfabricated particle sorting actuator of claim 1, wherein a ratio of a depth of the movable structure compared to a width is at least 1.2.

11. The microfabricated particle sorting actuator of claim 1, further comprising a transparent material disposed over the plurality of microfabricated fluidic channels, enclosing the fluid stream within the microfabricated fluidic channels.

12. A particle sorting system which sorts a target particle from other components of a fluid stream, comprising:
a detection region located in one of the microfabricated fluidic channels upstream of the microfabricated particle sorting actuator of claim 1; and
a detection system which generates a signal in response to the detection of a target particle within the detection region, wherein the microfabricated particle sorting actuator diverts the target particle into a particular one of the plurality of microfabricated fluidic channels when moving from a first position to a second position in response to the signal, and allows other particles to flow into another of the microfabricated fluidic channels.

13. The particle sorting system of claim 12, wherein the detection system uses a least one of a mechanical, optical, electrical, photovoltaic, magnetic, mass, hydrodynamic attributes of the particles to distinguish the target particle from other components of the fluid stream.

14. The particle sorting system of claim 12, wherein the detection system comprises at least one laser, at least one dichroic minor, and at least one optical detector, and wherein the target particle is identified by at least one of scattered incident light and a fluorescent tag which emits light when irradiated by the at least one laser.

15. The particle sorting system of claim 14, wherein the laser and the detector share an optical path which is oriented substantially perpendicularly to the plane.

16. The particle sorting system of claim 12, further comprising:
a source of magnetic flux positioned adjacent to the movable structure, but not mechanically coupled to the movable structure, which interacts with the movable structure to create a magnetic force between the movable structure and the source of magnetic flux, moving the movable structure from the first position to the second position which diverts the target particle.

17. The particle sorting system of claim 12, wherein the target particle is at least one of a cancer cell, a T-cell, a sperm cell and a stem cell.

18. The particle sorting system of claim 12, further comprising:
a disposable, self-contained cartridge which includes the microfabricated particle sorting actuator, fluidic channels, and the detection region, as well as a sample reservoir, a sort reservoir, and a waste reservoir.

* * * * *